(12) United States Patent
Chen et al.

(10) Patent No.: US 10,610,465 B2
(45) Date of Patent: *Apr. 7, 2020

(54) DELIVERY OF ACTIVE INGREDIENTS FROM PLANT MATERIALS TO SKIN

(71) Applicant: Mary Kay Inc., Addison, TX (US)

(72) Inventors: Daniel Chen, Shanghai (CN); James Swanzy, Arlington, TX (US)

(73) Assignee: Mary Kay Inc., Addison, TX (US)

( * ) Notice: Subject to any disclaimer, the term of this patent is extended or adjusted under 35 U.S.C. 154(b) by 80 days.

This patent is subject to a terminal disclaimer.

(21) Appl. No.: 16/041,322

(22) Filed: Jul. 20, 2018

(65) Prior Publication Data

US 2018/0344592 A1    Dec. 6, 2018

Related U.S. Application Data (63) Continuation of application No. 15/805,974, filed on Nov. 7, 2017, now Pat. No. 10,052,269, which is a continuation of application No. 14/572,272, filed on Dec. 16, 2014, now Pat. No. 9,839,589.

(60) Provisional application No. 61/917,205, filed on Dec. 17, 2013.

(51) Int. Cl.
| | | |
|---|---|---|
| *A61K 36/00* | (2006.01) | |
| *A61K 8/11* | (2006.01) | |
| *A61K 8/97* | (2017.01) | |
| *A61Q 19/00* | (2006.01) | |
| *A61K 9/00* | (2006.01) | |
| *A61K 9/70* | (2006.01) | |
| *A61F 13/00* | (2006.01) | |

(52) U.S. Cl.
CPC .......... *A61K 8/11* (2013.01); *A61F 13/00063* (2013.01); *A61K 8/97* (2013.01); *A61K 9/0014* (2013.01); *A61K 9/70* (2013.01); *A61Q 19/00* (2013.01); *A61K 36/00* (2013.01)

(58) Field of Classification Search
CPC .................................................... A61K 36/00
USPC ........................................................ 424/725
See application file for complete search history.

(56) References Cited

U.S. PATENT DOCUMENTS

| | | |
|---|---|---|
| 4,685,911 A | 8/1987 | Konno et al. |
| 4,747,841 A | 5/1988 | Kuratomi et al. |
| 4,755,384 A | 7/1988 | Mallasz |
| 5,456,055 A | 10/1995 | Boulanger et al. |
| 5,564,263 A | 10/1996 | Boulanger et al. |
| 5,597,580 A | 1/1997 | Sickler, Jr. |
| 6,156,323 A | 12/2000 | Verdicchio et al. |
| 6,190,710 B1 | 2/2001 | Nir et al. |
| 6,289,889 B1 | 9/2001 | Bell et al. |
| 6,451,331 B1 | 9/2002 | Slavtcheff et al. |
| 6,475,513 B1 | 11/2002 | Yamada |
| 6,610,312 B2 | 8/2003 | Farrell et al. |
| 6,833,486 B1 | 12/2004 | Eiselen |
| 6,878,380 B2 | 4/2005 | Farrell et al. |
| 6,906,017 B1 | 6/2005 | Sonnergren et al. |
| 6,919,089 B2 | 7/2005 | Bergquist |
| 7,427,417 B2 | 9/2008 | Jendrucko et al. |
| 8,377,215 B2 | 2/2013 | Gee et al. |
| 2003/0003136 A1 | 1/2003 | Bergquist |
| 2003/0194426 A1 | 10/2003 | Wendel et al. |
| 2004/0166145 A1 | 8/2004 | Burnett et al. |
| 2005/0053643 A1 | 3/2005 | Chen |
| 2005/0152954 A1 | 7/2005 | Farrell et al. |
| 2005/0207982 A1 | 9/2005 | Jendrucko et al. |
| 2007/0023048 A1 | 2/2007 | Cho |
| 2009/0286437 A1 | 11/2009 | Cunningham et al. |
| 2010/0300464 A1 | 12/2010 | Gee et al. |
| 2011/0064787 A1 | 3/2011 | Cabados |
| 2011/0177141 A1 | 7/2011 | Celeste |
| 2012/0209362 A1 | 8/2012 | Meneses |

FOREIGN PATENT DOCUMENTS

| | | |
|---|---|---|
| CN | 1172426 | 2/1998 |
| CN | 1422230 | 6/2003 |
| CN | 1684872 | 10/2005 |
| CN | 201147259 | 11/2008 |
| CN | 202881234 | 4/2013 |
| KR | 1020080033668 | 10/2009 |
| KR | 10-1244429 | 3/2013 |
| WO | WO 2001/70591 | 9/2001 |
| WO | WO 2004/033303 | 4/2004 |
| WO | WO 2012/135337 | 10/2012 |

OTHER PUBLICATIONS

Office Action issued in corresponding Chinese Patent Application No. 201480069342.7, dated Aug. 29, 2018.
International Search Report issued in PCT/US2014/070634, dated Mar. 27, 2015.

*Primary Examiner* — Michael V Meller
(74) *Attorney, Agent, or Firm* — Norton Rose Fulbright US LLP (57) ABSTRACT

Disclosed is an apparatus and methods for its use that is configured to be used to treat various skin conditions. The apparatus includes a water-permeable absorbent material and a plant material comprising a water-soluble skin-active ingredient. The plant material is enclosed within the water-permeable absorbent material, and the water-permeable absorbent material is configured to absorb water and allow the absorbed water to contact the plant material so as to release the active ingredient from the plant material. The active ingredient is then absorbed by the absorbent material, which is then topically applied to skin in need of skin treatment.

14 Claims, 3 Drawing Sheets

DELIVERY OF ACTIVE INGREDIENTS FROM PLANT MATERIALS TO SKIN

CROSS REFERENCE TO RELATED APPLICATIONS

This application is a continuation of U.S. application Ser. No. 15/805,974, filed Nov. 7, 2017, which is a continuation of U.S. application Ser. No. 14/572,272, filed Dec. 16, 2014 (issued as U.S. Pat. No. 9,839,589), which claims the benefit of U.S. Provisional Application Ser. No. 61/917,205, filed Dec. 17, 2013. The contents of the referenced applications are incorporated into the present application by reference.

BACKGROUND OF THE INVENTION

A. Field of the Invention

The invention generally concerns a water-permeable absorbent material in which a plant material having a water-soluble skin-active ingredient is loaded therein. The material can be used to treat a variety of skin conditions after being subjected to water.

B. Description of Related Art

Plant extracts are widely used in skin care formulations. One problem that arises in using such products is that the active ingredients in the plant extracts may be unstable in the formulations. Also, such formulas are structured for topical application to skin and include a variety of other base-set of ingredients. The base-set of ingredients typically constitutes the overwhelming majority of ingredients in the formulations, which can dilute the effectiveness of the active ingredient from the plant extract. This results in product formulations that have unstable actives in relatively low or non-efficacious amounts. To exacerbate the situation, current product formulations oftentimes rely on the use of preservatives (e.g., parabens, chlorobutanol, a phenol, sorbic acid, thimerosal, etc.) to maintain the product formulations, which can add to the costs associated with producing such formulations.

SUMMARY OF THE INVENTION

A solution to the current problems associated with cosmetic formulations that rely on plant extracts as the active ingredients has been discovered. The solution resides in the use of dried plants that are loaded or encased within water-permeable absorbent material. The dried plants have water-soluble skin active ingredients that can be released from the plants upon contact with water. The released ingredients can then be absorbed by the absorbent material, which can then be contacted with skin that is in need of skin treatment. This allows the user to obtain relatively large amounts of active ingredients directly from the plant source rather than through a product formulation that has a limited amount of such actives. Further, the actives can be used immediately, thereby increasing the likelihood that the actives are used in their active form—i.e., the stability issues of the actives become irrelevant as they are not subjected to or stored in product formulations/vehicles. Even further, the manufacturer of such products can avoid the costs associated with preparing base formulations or vehicles for the actives. Rather, all that is needed is water, the plant material and the absorbent material.

In one embodiment of the present invention there is disclosed an apparatus configured to be used to treat a skin condition. The apparatus can include a water-permeable absorbent material and a plant material comprising a water-soluble skin-active ingredient or a powdered form of a water-soluble skin-active ingredient or a combination thereof. The powdered form of the active can also be water-insoluble. The plant material can be the whole plant or portion of the plant (e.g., stem, root, leaf, petal, flower, bud, bark, seed, fruit or pulp, etc.). The plant material used in the context of the present invention is from the plant and not an extract or isolated ingredient from the plant—for example, the material can be leaves from a plant, roots from a plant, stems from a plant, petals or flowers from a plant, bark from a plant, buds from a plant, seeds from a plant, fruit or pulp from a plant). In some instances, the apparatus consists or consists essential of the plant material and the water-permeable absorbent material (i.e., it does not include other skin actives, isolated actives, extracts, base-set of ingredients, etc.). The plant material can be processed such that it is dried or dehydrated or lyophilized, which can further increase the stability of the plant material. Also, the plant material can be chopped, crushed, powdered, micronized, etc., which can further increase the surface area of the plant. An increase in the surface area of the material can increase the amount of active released from the plant once contacted with water. Similarly, the powdered or particulate form of the skin active can be the same active present in the plant or a different active altogether. In particular instances, the powdered or particulate active can be a vitamin (e.g., vitamin C or vitamin E or salts thereof). The plant or powdered form of the skin-active can be enclosed or encased or stitched into the water-permeable absorbent material. Further, the water-permeable absorbent material can be configured such that it absorbs water and allows the absorbed water to contact the plant material or the powdered form of the skin-active ingredient so as to release the skin active material from the plant or solubilize the skin active materials. The released or solubilized skin active ingredients can then be absorbed by the absorbent material. The absorbent material can then be contacted with skin in need of treatment. In some instances, the water-permeable absorbent material can include a first outer surface and an opposing second outer surface, with the plant material or the powdered skin-active ingredient disposed between said surfaces. The surfaces can be formed from a single piece of material such as by folding the material over to create a pocket or space for the plant material or powdered active. The material can be stitched or otherwise sealed together to prevent exit of the plant material or powdered active. In other instances, the surfaces can be formed from at least two separate pieces of materials that are stitched or otherwise sealed together to form said pocket or cavity for the plant material or powdered active. In either instance, the first outer surface can be configured to have a greater surface roughness when compared with the surface roughness of the second outer surface. The first outer surface can be used to exfoliate or cleanse skin, while the second outer surface can be configured to not exfoliate skin—e.g., it can be used to rinse skin or wash skin or apply additional actives to the skin once it has been exfoliated. The surface roughness can be increased by using a material that is different from the second surface. Alternatively, the surface roughness can be increased by incorporating beads or other raised elements into the first surface. In either instance, the surface roughness can be determined subjectively by touching said surfaces to determine which surface feels rougher. Alternatively, the surface roughness can be determined objectively such as by using a Kawabata Evaluation System FB4 Surface Tester, which can measure the surface properties of friction (resistance/drag) and surface contour (roughness). In other aspects, the first and second outer surfaces have substantially the same surface roughness. The water content of the apparatus prior to use can be less than 5, 4, 3, 2, or 1% or can be substantially anhydrous (i.e., less than 1% by weight of water in the absorbent material and plant material). This allows for a lighter product and can contribute to the stability of the plant material or powdered active. In particular instances, the apparatus is shaped so as to conform to a specific area of skin. For instance, facial skin has several areas ranging from the forehead, nose, cheeks, skin around the eyes, chin, skin above the lip and below the nose, etc. The apparatus can be shaped to substantially conform with or match the shape of a given facial area. Also, the face has been categorized into various zones or regions, such as the T-zone region (which includes the forehead and nose), the S-zone region (which includes each cheek), the O-zone region (which includes the chin and skin above the lip), and the eye area region (which includes skin directly above and below the eyes). The apparatus can be shaped to substantially conform with or match the shape of a given zone or region. This allows for targeted treatment of a given skin condition in a given zone or region (e.g, oily skin in the T-Zone region) without treating other areas or skin zones. In addition the apparatus can be shaped for other skin areas such as the neck region, the décolleté region, the hands, the feet, etc. Also, the apparatus does not need to have a preservative, as the plant material or the powdered active can be dried or lyophilized prior to use. Therefore, preservatives such as parabens (e.g., methylparaben, propylparaben, combinations thereof), chlorobutanol, a phenol, sorbic acid, thimerosal, etc. can be excluded/not used with the apparatus. Further, multiple plant materials and multiple plant parts can be incorporated into a given apparatus. Such combinations can be used to tailor or design a given apparatus to a specific skin condition. Non-limiting examples of skin conditions include acne, symptoms associated with acne (e.g., presence of open or closed comedones, papules, pustules, nodulocystic lesions, skin redness, etc.), pruritus, spider veins, lentigo, discolored skin (e.g, age spots or dark spots, senile purpura, keratosis, melasma, hyperpigmentation), fine lines or wrinkles, nodules, sun damaged skin, dermatitis (including, but not limited to seborrheic dermatitis, nummular dermatitis, contact dermatitis, atopic dermatitis, exfoliative dermatitis, perioral dermatitis, and stasis dermatitis), psoriasis, folliculitis, rosacea, impetigo, erysipelas, erythrasma, eczema, and other inflammatory skin conditions. In certain non-limiting aspects, the skin condition can be caused by exposure to UV light, age, irradiation, chronic sun exposure, environmental pollutants, air pollution, wind, cold, heat, chemicals, disease pathologies, smoking, or lack of nutrition. The skin can be facial skin or non-facial skin (e.g., arms, legs, hands, chest, back, feet, etc.). In particular embodiments, the skin condition can be fine lines or wrinkles, discolored skin, hyperpigmented skin, uneven skin tone, acne, oily skin, dry skin, or reddened or erythemic skin.

Also disclosed is a method of treating a skin condition (such as one of those noted above) with any one of the apparatus's of the present invention. The method can include subjecting the apparatus to water for a sufficient period of time so as to release the water-soluble active ingredient from the plant material or solubilize the active ingredient and to allow said active ingredient to be absorbed by the water-permeable absorbent material, and contacting the water-permeable absorbent material to skin in need of treatment. The apparatus can be fully immersed in water, partially immersed in water, or simply wetted with water. The absorbent material with the absorbed active can be applied to a fine line or wrinkle, or to hyperpigmented or discolored skin, or to skin having uneven skin tone, or to acne, or to dry skin, or to oily skin, or to reddened or erythemic skin, or to any of the aforementioned skin conditions listed in the above paragraph. Therefore, the apparatus of the present invention can be used to treat a wide range of skin conditions by tailoring the plant material to a given skin condition. In particular instances, the water used to release the actives from the plant material or to solubilize the actives is room temperature (i.e., 20 to 25° C.). In other instances, the water can be heated (e.g., 30° C. to 100° C.) prior to contacting the skin. The amount of time that the apparatus is subjected to water can be modified as desired, with longer soak times equating to more actives being released and absorbed by the absorbent material. In some instances, the time period can range from 1 minute to 60 minutes or from 1 minute to 30 minutes or from 10 to 30 minutes.

Also disclosed in the context of the present invention are embodiments 1 to 31. Embodiment 1 is an apparatus configured to be used to treat a skin condition, the apparatus comprising: (a) a water-permeable absorbent material; and (b) a plant material comprising a water-soluble skin-active ingredient or a powdered form of a water-soluble skin-active ingredient or a combination thereof, wherein the plant material or the powdered form of the skin-active ingredient is enclosed within the water-permeable absorbent material, and wherein the water-permeable absorbent material is configured to absorb water and allow the absorbed water to contact the plant material or the powdered form of the skin-active ingredient so as to release or solubilize the skin-active ingredient and allow the skin-active ingredient to be absorbed by the absorbent material. Embodiment 2 is the apparatus of embodiment 1, wherein the water-permeable absorbent material comprises a first outer surface and an opposing second outer surface, with the plant material or the powdered skin-active ingredient disposed between said surfaces. Embodiment 3 is the apparatus of embodiment 2, wherein the first outer surface has a greater surface roughness when compared with the surface roughness of the second outer surface, such that the first outer surface is configured to exfoliate skin, and the second outer surface is configured to not exfoliate skin. Embodiment 4 is the apparatus of embodiment 2, wherein the first outer surface and the second outer surface have substantially the same surface roughness. Embodiment 5 is the apparatus of any one of embodiments 1 to 4, wherein the plant material is dried plant material. Embodiment 6 is the apparatus of any one of embodiments 1 to 5, wherein the water content of the apparatus is less than 1% by weight of the apparatus or wherein the apparatus is substantially anhydrous. Embodiment 7 is the apparatus of any one of embodiments 1 to 6, wherein the apparatus is shaped to substantially correspond to T-zone region of facial skin. Embodiment 8 is the apparatus of any one of embodiments 1 to 6, wherein the apparatus is shaped to substantially correspond to an S-zone region of facial skin. embodiment 9 is the apparatus of any one of embodiments 1 to 6, wherein the apparatus is shaped to substantially correspond to the O-zone region of facial skin. Embodiment 10 is the apparatus of any one of embodiments 1 to 6, wherein the apparatus is shaped to substantially correspond to the eye area region of facial skin. Embodiment 11 is the apparatus of any one of embodiments 1 to 6, wherein the apparatus is shaped to substantially correspond to the décolleté region of a person's skin. Embodiment 12 is the apparatus of any one of embodiments 1 to 6, wherein the apparatus is shaped to substantially correspond to the forehead region, cheek region, nose region, or chin region of a person's skin. Embodiment 13 is the apparatus of any one of embodiments 1 to 12, wherein a preservative is not enclosed within the water-permeable absorbent material or wherein the apparatus does not include a preservative. Embodiment 14 is the apparatus of embodiment 13, wherein the apparatus does not include a preservative such as a paraben, chlorobutanol, a phenol, sorbic acid, or thimerosal. Embodiment 15 is the apparatus of any one of embodiments 1 to 14, wherein the plant material is enclosed within the water-permeable absorbent material. Embodiment 16 is the apparatus of any one of embodiments 1 to 14, wherein the powdered form of the skin-active ingredient is enclosed within the water-permeable absorbent material. Embodiment 17 is the apparatus of any one of embodiments 1 to 14, wherein the plant material and the powdered form of the skin-active ingredient are both enclosed within the water-permeable absorbent material. Embodiment 18 is the apparatus of any one of embodiments 1 to 17, wherein the water-soluble active ingredient is configured to treat fine lines or wrinkles. Embodiment 19 is the apparatus of any one of embodiments 1 to 17, wherein the water-soluble active ingredient is configured to treat hyperpigmented or discolored skin. Embodiment 20 is the apparatus of any one of embodiments 1 to 17, wherein the water-soluble active ingredient is configured to treat acne. Embodiment 21 is the apparatus of any one of embodiments 1 to 17, wherein the water-soluble active ingredient is configured to treat oily skin or dry skin. Embodiment 22 is the apparatus of any one of embodiments 1 to 21, wherein the apparatus is steeped in water, and wherein the water-soluble active ingredient is absorbed by the water-permeable absorbent material. Embodiment 23 is the apparatus of any one of embodiments 1 to 22, wherein the powdered form of the skin active is ascorbic acid or a derivative thereof. Embodiment 24 is a method of treating skin, comprising placing any one of the apparatus's of embodiments 1 to 23 in water for a sufficient period of time so as to release the water-soluble active ingredient from the plant material or solubilize said active ingredient and to allow said active ingredient to be absorbed by the water-permeable absorbent material, and contacting the water-permeable absorbent material having the absorbed active to skin in need of treatment. Embodiment 25 is the method of embodiment 24, wherein the water-permeable absorbent material is applied to a fine line or wrinkle. Embodiment 26 is the method of embodiment 24, wherein the water-permeable absorbent material is applied to hyperpigmented or discolored skin. Embodiment 27 is the method of embodiment 24, wherein the water-permeable absorbent material is applied to oily skin or dry skin. Embodiment 28 is the method of embodiment 24, wherein the water-permeable absorbent material is applied to acne. Embodiment 29 is the method of any one of embodiments 24 to 28, wherein the water is room temperature. Embodiment 30 is the method of any one of embodiments 24 to 28, wherein the water is heated to 30° C. to 100° C. prior to contacting the skin. Embodiment 31 is the method of any one of embodiments 24 to 30, wherein the sufficient period of time ranges from 1 minute to 60 minutes or from 1 minute to 30 minutes or from 10 to 30 minutes.

It is contemplated that any embodiment discussed in this specification can be implemented with respect to any method or composition of the invention, and vice versa. Furthermore, compositions of the invention can be used to achieve methods of the invention.

The terms "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the phrase "consist essentially of," a basic and novel characteristic of the present invention is that skin conditions can be treated without utilizing a standard topical skin formulation such as an emulsion, gel, lotion, or cream.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

BRIEF DESCRIPTION OF THE DRAWINGS

The following drawings illustrate by way of example and not limitation. For the sake of brevity and clarity, every feature of a given structure may not be labeled in every figure in which that structure appears. Identical reference numbers do not necessarily indicate an identical structure. Rather, the same reference number may be used to indicate a similar feature or a feature with similar functionality, as may non-identical reference numbers. The figures are not drawn to scale.

DETAILED DESCRIPTION OF THE INVENTION

Figure 2:
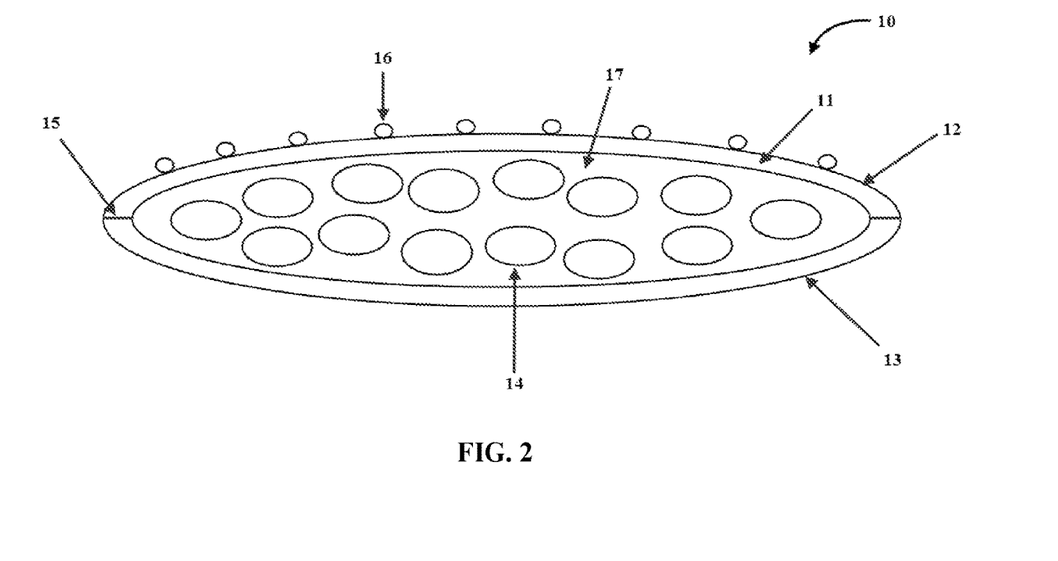
FIG. 2 is a cross-sectional view of an apparatus of the present invention.

FIG. 2 provides a non-limiting aspect of one apparatus 10 of the present invention. The apparatus 10 can include a water-permeable absorbent material 11, which includes a first surface 12 and a second surface 13. This material 11 can be formed from a natural or synthetic cloth or fabric, sponge, foam, mesh plastic, mesh vinyl, mesh metal, mesh fabric, a paper product, or any other material that can absorb water. Further, the material 11 can be naturally permeable to water (e.g., sponge, cloth, etc.) or can be made permeable through introduction of pores or holes in the first 12 or second 13 surfaces or both surfaces of the material 11. In preferred aspects, the material 11 is made from a sponge or cloth or foam. The water-permeable absorbent material can be configured such that an inner cavity or space 17 is created, which can be used to hold plant material 14 or powdered water-soluble active ingredients or both. In this embodiment, the material 14 is plant material that has been dried and prepared into particulate or powdered form. The process used to prepared the plant material 14 can include obtaining the whole plant or any part thereof of (e.g., leaves, stems, bark, roots, fruit, flowers or flower buds, seeds, seed pods, sap, whole plant, etc.). The desired part of the plant or the whole plant is crushed up (e.g., blender) and then subjected to a drying or lyophilized step to remove excess water moisture (e.g., drying at 50° C. for 12 hours). For active ingredients that have been lyophilized into a powder, a similar process can be used. In the embodiment in FIG. 2, the first surface 12 of the water-permeable absorbent material 11 is modified by inclusion of raised beads 16 so as to increase its surface roughness. The raised beads 16 can be plastic beads, silica beads, particulate sugar, etc. or any material that can increase the surface roughness. The beads 16 can be affixed to the first surface 12 through an adhesive material. In particular aspects, the first surface 12 having the raised beads 16 can be used to exfoliate skin, and the second surface 13 can be used to apply the absorbed active ingredient to the skin. In this embodiment, the water-permeable absorbent material 11 is configured such that the inner space or cavity 17 is created by folding the absorbent material 11 over onto itself to create said cavity 17. The cavity 17 can then be sealed by stitches 15. Other means of sealing the cavity 17 can also be used, such as by using adhesives, tying the materials together with a thread without using stitches, etc. Even further, two separate pieces of water-permeable absorbent material can be stitched or otherwise adhered together to form the apparatus 10. In some embodiments, the first water-permeable absorbent material can be non-permeable to water and can have an increased surface roughness so as to exfoliate or cleanse skin. The second water-permeable absorbent material can be water permeable and can be used to apply the absorbed active to skin.

Once the apparatus 10 is placed into a liquid environment that includes water, the water-permeable absorbent material 11 will absorb the water. Water will then enter the inner cavity 17 and come into contact with the plant material 14 or powdered active. This will allow the water-soluble active ingredient within the plant material 14 to be released and then absorbed into the absorbent material 11. Alternatively, the powdered active can be solubilized within the water and absorbed by the absorbent material 11. In either instance, once the water-soluble active is absorbed, the absorbent material 11 can then be used to contact skin that needs treatment with said water-soluble active.

Figure 1:
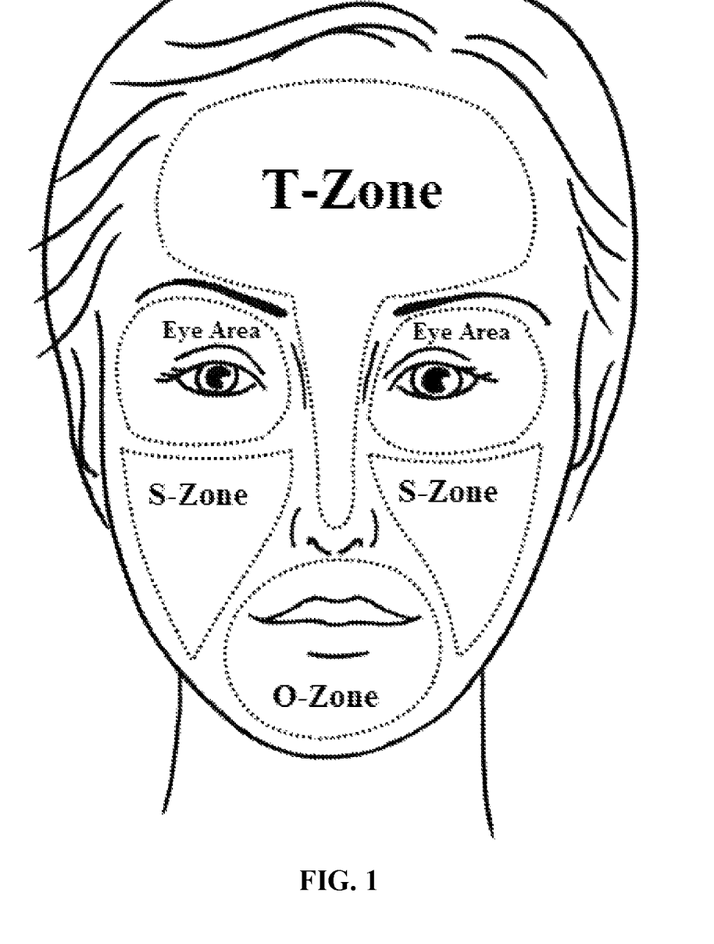
FIG. 1 is an illustration of the various regions of a person's face.

Referring to FIG. 1, this figure illustrates the various zones or regions of the face. The apparatus 10 of the present invention can be shaped to substantially match the shape of a given zone illustrated in FIG. 1. The zones include the T-zone (which includes the forehead and nose), the S-zone region (which includes each cheek), the O-zone region (which includes the chin and skin above the lip), and the eye area region (which includes skin directly above and below the eyes). This allows for targeted treatment of a given skin condition in a given zone or region (e.g, oily skin in the T-Zone region) without treating other areas or skin zones. Alternatively, the apparatus 10 can be shaped such that the entire face is covered by the apparatus rather than a targeted zone. In addition the apparatus 10 can be shaped for other skin areas such as the neck region, the décolleté region, the hands, the feet, etc.

With respect to the plant material 14 that can be used in the contact of the present invention, any type of such material 14 is contemplated. This allows for the apparatus 10 to be configured or designed for specific skin conditions. For instance, plant material 14 that is known to treat fine lines and wrinkles or treat uneven skin tone or dry skin or oily skin or acne or any other skin condition can be used. Examples of such plant materials is provided in the Example section of this application and incorporated into the present application by reference. Other non-limiting examples include plant materials obtained from any of the following: *Nymphaea gigantea; Syzygium moorei; Cupaniopsis anacardioides; Archidendron hendersonii; Tristaniopsis laurina; Brachychiton acerifolius; Stenocarpus sinuatus; Alphitonia excelsa; Eucalyptus coolabah; Plumeria alba; Cocos nucifera; Tamarindus indica; Matricaria recutita* (chamomile); *Coffea arabica*; Amaryllidaceae; Anacardiaceae; Anonaceae (ylang-ylang); Apiaceae (dill, *angelica*, coriander, sea fennel, carrot, parsley); Araceae; Aristolochiaceae; Asteraceae (achillea, artemisia, helichrysum); Betulaceae; Brassicaceae; Burseraceae (incense); Caryophyllaceae; Canellaceae; Cesalpiniaceae (copaiba balsam); Chenopodaceae; Cistaceae (cistus); Cyperaceae; Dipterocarpaceae; Ericaceae (gaultheria); Euphorbiaceae; Fabaceae; Geraniaceae (geranium); Guttiferae; Hamamelidaceae; Hernandiaceae; Hypericaceae (St John's wort); Iridaceae; Juglandaceae; Lamiaceae (thyme, oregano, monarda, savory, basil, marjorams, mints, patchouli, lavenders, sages, lemon catnip, rosemary, hyssop, balm, rosemary); Lauraceae (ravensara, laurel, rosewood, cinnamon, litsea); Liliaceae (garlic); Magnoliaceae (magnolia); Malvaceae; Meliaceae; Monimiaceae; Moraceae (hemp, hop); Myricaceae; Mysristicaceae: (nutmeg); Myrtaceae (eucalyptus, tea tree, paperbark tree, cajuput, backhousia, clove, myrtle); Oleaceae; Piperaceae (pepper); Pittosporaceae; Poaceae (citronella, lemongrass, vetiver); Polygonaceae; Renonculaceae; Rosaceae (roses); Rubiaceae; Rutaceae (all citrus plants); Salicaceae; Santalaceae (sandalwood); Saxifragaceae; Schisandraceae; Styracaceae (benj oin); Thymelaceae (agar wood); Tilliaceae; Valerianaceae (valerian, spikenard); Verbenaceae (lantana, verveine); Violaceae; Zingiberaceae (galangal, curcuma, cardamom, ginger); Zygophyllaceae; soy; aloe vera; or any combination thereof.

Also, and as indicated above, the apparatus 10 can include powdered or particulate actives. In preferred aspects, the actives are water-soluble as they may be more easily absorbed into the absorbent material 11. However, water insoluble active can also be used, as the water can be dispersed within the water and then absorbed by the material 11. Non-limiting examples of such actives that can be obtained in powdered or particulate form include vitamins (e.g., vitamin C, vitamin A, vitamin E, retinol, tretinoin, and salts or esters thereof), caffeine, salicylic acid, benzoyl peroxide, alpha-hydroxy acids such as, for example, lactic acid or citric acid, hydroquinone, kojic acid, hyaluronic acid, alpha-lipoic acid, an antioxidant, a flavonoid, an analgesic, an antibacterial, an anthocyanin, or any combination thereof. Additionally, essential oils can be included in capsule or tablet form, in which the capsule or tablet breaks down or releases the oil after being contacted with water. Essential oils can impart a pleasant fragrance to the apparatus 10 of the present invention. Non-limiting examples of essential oils include sesame oil, macadamia nut oil, tea tree oil, evening primrose oil, Spanish sage oil, Spanish rosemary oil, coriander oil, pimento berry oil, camphor oil, eucalyptus oil, cinnamon oil, jojoba oil, oil of wintergreen, lemon oil, orange oil, oil of clove, or any combination thereof.

Further, while water is preferred in the context of the present invention, the apparatus 10 can be contacted with other liquids such as an alcohol, glycolic mixtures, or combinations thereof that can further include water. However, and again, water is preferred, as it is readily available to the end user.

The water contacting step may be performed in any way suitable to provide effective extraction, dissolution, or dispersion of ingredients within the container. For example, the container may be fully immersed in the water, the container may be only partly immersed in the water, or the container may be wetted by the water but not immersed.

In the above description, numerous specific details are provided to provide a thorough understanding of the disclosed embodiments. One of ordinary skill in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Other objects, features and advantages of the present invention will become apparent from the above detailed description. It should be understood, however, that the detailed description, while indicating specific embodiments of the invention, are given by way of illustration only. Additionally, it is contemplated that changes and modifications within the spirit and scope of the invention will become apparent to those skilled in the art from this detailed description.

The claims are not to be interpreted as including means-plus- or step-plus-function limitations, unless such a limitation is explicitly recited in a given claim using the phrase(s) "means for" or "step for," respectively.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Materials and Methods for Obtaining Extracts

Figure 3:
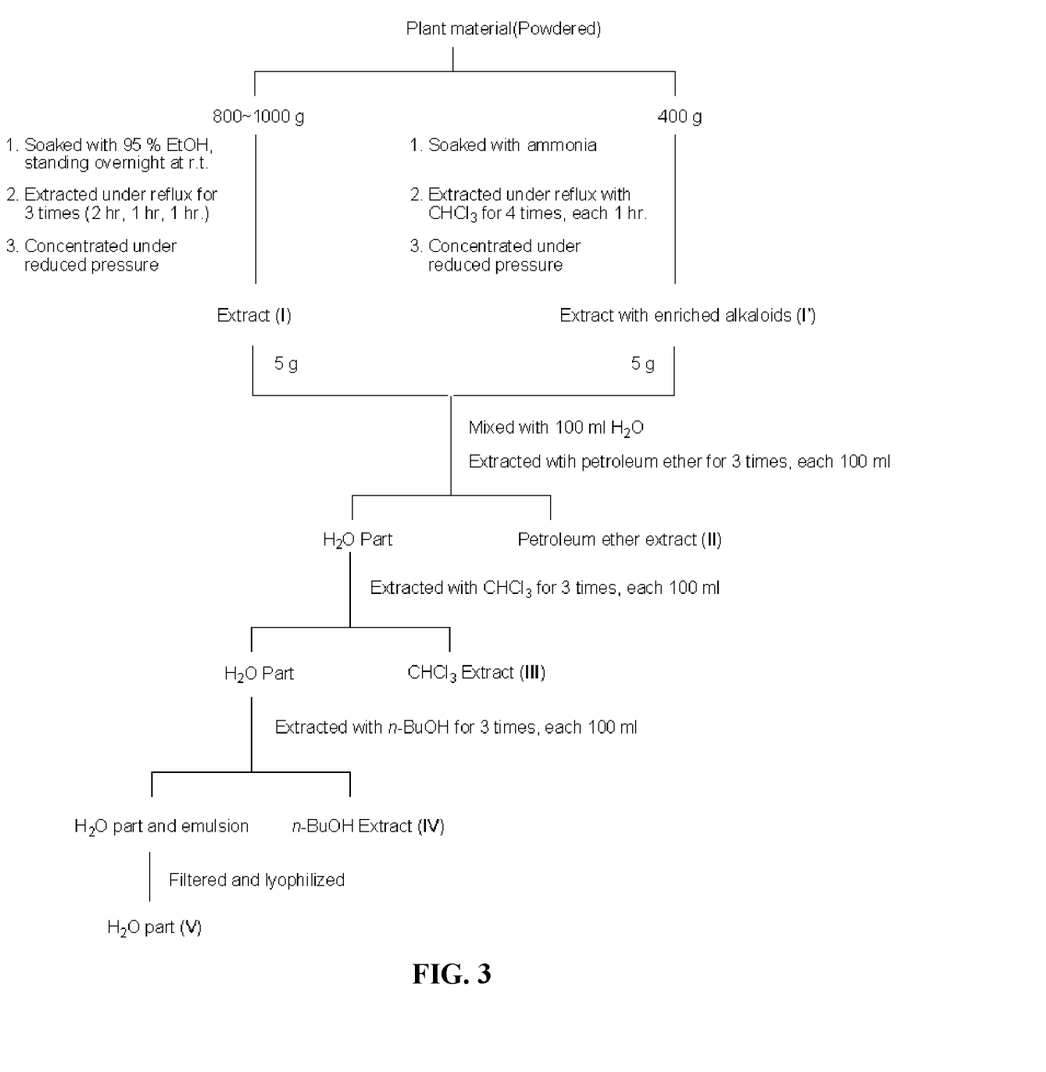
FIG. 3 Extraction process used to obtain extracts from various plant materials.

The extracts identified in Table 1 were prepared from the whole plant. Each plant was individually obtained, ground, and dried, to produce a powder. The powder was treated according to the process described in FIG. 3. These extracts are provided in International Publication WO 2012/135337.

Example 2

Efficacy of Extracts

Each extract prepared according to the process described in Example 1 was subjected to a variety of assays to determine their skin efficacy. The following Table 1 provides a summary of these data. A description of the assays used to obtain these data is provided below Table 1.

TABLE 1

| Plant Extract | B16 Inhibition | Collagen Stimulated | TNF-α Inhibition | AO Activity | Tyrosinase Inhibition |
|---|---|---|---|---|---|
| Oenothera rosea | | | −80.518 | −89.54 | −28.88 |
| Salvia plebeia | | | −42.301 | | −29.22 |
| Elaeagnus lanceolatus | | | −67.626 | −64.13 | −30.22 |
| Docynia delavayi | | | −47.542 | −63.79 | |
| Alternanthera philoxeroides | | | −35.971 | −10.42 | −28.38 |
| Pyrus pyrifolia | | | −20.682 | −87.03 | |
| Datura stramonium | | 61.885 | −44.465 | −26.97 | −24.78 |
| Picris hieracioides ssp. Japonica | | 29.806 | −62.551 | −29.68 | −26.82 |
| Phoebe neurantha | | | −29.541 | −90.49 | −29.37 |
| Acanthopanax gracilistylus | | | −13.25 | −43.66 | −17.62 |
| Osmanthus fragrans | | 35.271 | −65.592 | −74.75 | −21.07 |
| Michelia chapensis | | | −78.229 | −61.21 | −21.2 |
| Rhododendron spinuliferum | | | −81.961 | −91.53 | −39.34 |
| Dendrobenthamia capitata | | | −54.07 | −89.32 | −33.33 |
| Ficus microcarpa | | | −87.697 | −89.96 | −48.02 |
| Vitex negundo | | | | −62.44 | −17.62 |
| Sequoia sempervirens | | | −89.127 | −90.39 | −44.19 |
| Cassia surattensis | | | | −61.48 | |
| Hypericum forrestii | | | | −90.61 | −34.23 |
| Ficus pumila | | | | −45.41 | −27.84 |
| Cercis chinensis | | | | −87.44 | |
| Rhododendron decorum | | | −80.98 | −89.62 | −18.16 |
| Ficus retusa ssp. nitida | | | −82.99 | −81.43 | −18.64 |
| Berchemia polyphylla var. leioclada | | | | −85.34 | −20.79 |
| Elaeocarpus decipiens | | | −85.14 | −90.55 | −25.69 |
| Quercus variabilis | | | −89.098 | −88.76 | −39.43 |
| Prunus serrulata | | | −48.995 | −55.23 | |
| Melastoma normale | | | −89.969 | −90.18 | −42.53 |
| Lycium chinensis | | 64.232 | −23.234 | −71.92 | −24.85 |
| Chamaecyparis pisifera | | | −75.879 | −84.61 | −33.57 |
| Millettia dielsiana | | 63.307 | −55.654 | −80.51 | −24.01 |
| Plumbago auriculata | | | −82.659 | −87.81 | −35.48 |
| Nandina domestica | | | −68.886 | −53.51 | −20.07 |
| Smilax bockii | | | −51.522 | −69.3 | |
| Schima wallichii | | | −85.116 | −90.58 | −49 |
| Thevetia peruviana | | | −66.222 | −24.03 | −19.26 |
| Carissa spinarum | | | −55.148 | −87.7 | — |
| Maesa perlarius | | | −51.022 | −13.7 | −22.58 |
| Wisteria floribunda | | 64.976 | −16.421 | −32.56 | |
| Schima argentea | | | −56.387 | −29.44 | −23.51 |
| Acacia decurrens var. dealbata | | | −94.503 | −89.06 | −36.25 |
| Viburnum ichangense | | 43.022 | −93.66 | −87.08 | −25.37 |
| Conyza sumatrensis | | 60.463 | −65.007 | −21.11 | −22.31 |
| Lantana camara | | | | −75.885 | −85.35 |

TABLE 1-continued

| Plant Extract | B16 Inhibition | Collagen Stimulated | TNF-α Inhibition | AO Activity | Tyrosinase Inhibition |
|---|---|---|---|---|---|
| Euonymus bungeanus | | | −73.908 | −72.57 | −26.96 |
| Loropetalum chinensis var. rubrum* | | | −85.4 | −88.38 | −49.8 |
| Jasminum mesnyi | | | −64.987 | −29.23 | −22.58 |
| Stellaria saxatilis | | | −70.043 | | −20.58 |
| Elscholtzia cypriani | | | −86.121 | −38.27 | −17.89 |
| Daucus carota | | | −75.219 | | −22.65 |
| Bougainvillea glabra | | | −55.624 | | −24.45 |
| Serissa serissoides | | | −51.755 | −30.05 | −16.09 |
| Antidesma acidum | | | −88.413 | −84.91 | −45.82 |
| Sargentodoxa cuneata | | | −90.12 | −90.82 | −31.79 |
| Ajuga forrestii* | | | −60.514 | −17.91 | −12.1 |
| Terminalia chebula | | | −88.998 | −91.26 | −38.1 |
| Paederia scandens | | | −64.966 | −27.33 | −22.52 |
| Lonicera japonica | | | −15.155 | −64.62 | −16.22 |
| Achyranthes bidentata | | 48.53 | −66.995 | | −19.05 |
| Hedera nepalensis | | | −58.104 | −23.45 | −18.53 |
| Canna chinensis | | | −76.392 | | −31.02 |
| Ephedra sinica | | | −93.275 | −87.36 | −53.67 |
| Dichlrocephala auriculata | −21.69 | | −80.436 | −25.39 | −18.65 |
| Prunus mume var. viridicalyx | | | −66.348 | −88.52 | |
| Castanea molissima | | | −74.369 | −89.19 | −33.1 |
| Elaeagnus bockii | | | −62.85 | −34.28 | |
| Parkia biglobosa | | | −46.022 | −54.37 | −15.29 |
| cinnamomum parthenoxylon | | | −83.774 | −88.6 | −23.98 |
| Euphorbia esula | | | −81.957 | −89.55 | −21.18 |
| Sauropus androgynus | −26.05 | | −73.638 | −86.99 | −28.33 |
| Chamaecrista mimosoides | | | −82.346 | −87.57 | −28.47 |
| Crotolaria zanzibarica | | | −83.556 | −29.92 | −13.74 |
| Castanopsis eyrei | | | −65.887 | | −15.71 |
| Phoenix roebelenii | −22.81 | | −67.826 | −87.57 | −34.78 |
| Vinca major | −23.84 | | −29.153 | −42.35 | |
| Swertia macrosperma | −27.26 | | −77.217 | −53.48 | |
| Onosma paniculatum | −26.25 | | −45.42 | | |
| Polygonum multiflorum | | | −57.213 | | |
| Gerbera jamesonii | −26.28 | | −33.293 | −48.86 | |
| Astragalus membranaceus | | | | | |
| Duranta repens | | | −59.57 | −73.8 | |
| Callicarpa macrophylla | | | −46.109 | −86.99 | |
| Livistona chinensis | −23.15 | | −89.63 | −70.39 | −17.01 |
| Incarvillea arguta | | | −66.723 | −21.13 | |
| Lepidium virginicum | | | −62.833 | −20.37 | −16.23 |
| Fagopyrum cymosum | 28.96 | | −59.044 | −59.26 | |
| Quercus rehderiana | | | −73.343 | −88.65 | −24.29 |
| Cunninghamia lanceolata | | | −91.893 | −84.34 | |
| Deutzia glomeruliflora | −21.36 | | −35.277 | −57.02 | |

**Both *Ajuga forrestii* and *Loropetalum chinensis* extracts were also found to stimulate collagen I synthesis in the skin by the Collagen Stimulation Assay described below B16 Melanogenesis Assay:

Melanogenesis is the process by which melanocytes produce melanin, a naturally produced pigment that imparts color to skin, hair, and eyes. Inhibiting melanogenesis is beneficial to prevent skin darkening and lighten dark spots associated with aging. This bioassay utilizes B16-F1 melanocytes (ATCC), an immortalized mouse melanoma cell line, to analyze the effect of compounds on melanogenesis. The endpoint of this assay is a spectrophotometric measurement of melanin production and cellular viability. B16-F1 melanocytes, cultivated in standard DMEM growth medium with 10% fetal bovine serum (Mediatech) at 37° C. in 10% $CO_2$, were treated with each of the extracts identified in Table 1 for 6 days. Following incubation, melanin secretion was measured by absorbance at 405 nm and cellular viability was quantified.

Collagen Stimulation Assay:

Collagen is an extracellular matrix protein critical for skin structure. Increased synthesis of collagen helps improve skin firmness and elasticity. This bioassay analyzes the effect of extracts on the production of procollagen peptide (a precursor to collagen) by human epidermal fibroblasts. The endpoint of this assay is a spectrophotometric measurement that reflects the presence of procollagen peptide and cellular viability. The assay employs the quantitative sandwich enzyme immunoassay technique whereby a monoclonal antibody specific for procollagen peptide has been pre-coated onto a microplate. Standards and samples are pipetted into the wells and any procollagen peptide ☐present is bound by the immobilized antibody. After washing away any unbound substances, an enzyme-linked polyclonal antibody specific for procollagen peptide is added to the wells. Following a wash to remove any unbound antibody-enzyme reagent, a substrate solution is added to the wells and color develops in proportion to the amount of procollagen peptide bound in the initial step using a microplate reader for detection at 450 nm. The color development is stopped and the intensity of the color is measured.

Subconfluent normal human adult epidermal fibroblasts (Cascade Biologics) cultivated in standard DMEM growth medium with 10% fetal bovine serum (Mediatech) at 37° C. in 10% $CO_2$, were treated with each of the extracts identified in Table 1 for 3 days. Following incubation, cell culture medium was collected and the amount of procollagen peptide secretion quantified using a sandwhich enzyme linked immuno-sorbant assay (ELISA) from Takara (#MK101).

Tumor Necrosis Factor Alpha (TNF-α) Assay:

The prototype ligand of the TNF superfamily, TNF-α, is a pleiotropic cytokine that plays a central role in inflammation. Increase in its expression is associated with an up regulation in pro-inflammatory activity. This bioassay analyzes the effect of extracts on the production of TNF-α by human epidermal keratinocytes. The endpoint of this assay is a spectrophotometric measurement that reflects the presence of TNF-α and cellular viability. The assay employs the quantitative sandwich enzyme immunoassay technique whereby a monoclonal antibody specific for TNF-α has been pre-coated onto a microplate. Standards and samples are pipetted into the wells and any TNF-α ☐present is bound by the immobilized antibody. After washing away any unbound substances, an enzyme-linked polyclonal antibody specific for TNF-α is added to the wells. Following a wash to remove any unbound antibody-enzyme reagent, a substrate solution is added to the wells and color develops in proportion to the amount of TNF-α bound in the initial step using a microplate reader for detection at 450 nm. The color development is stopped and the intensity of the color is measured.

Subconfluent normal human adult keratinocytes (Cascade Biologics) cultivated in EpiLife standard growth medium (Cascade Biologics) at 37° C. in 5% $CO_2$, were treated with phorbol 12-myristate 13-acetate (PMA, 10 ng/ml, Sigma Chemical, #P1585-1MG) and each of the extracts identified in Table 1 for 6 hours. PMA has been shown to cause a dramatic increase in TNF-α secretion which peaks at 6 hours after treatment. Following incubation, cell culture medium was collected and the amount of TNF-α secretion quantified using a sandwich enzyme linked immuno-sorbant assay (ELISA) from R&D Systems (#DTA00C).

Antioxidant (AO) Assay:

An in vitro bioassay that measures the total anti-oxidant capacity of an extract. The assay relies on the ability of antioxidants in the sample to inhibit the oxidation of ABTS® (2,2'-azino-di-[3-ethylbenzthiazoline sulphonate]) to ABTS®+ by metmyoglobin. The antioxidant system of living organisms includes enzymes such as superoxide dismutase, catalase, and glutathione peroxidase; macromolecules such as albumin, ceruloplasmin, and ferritin; and an array of small molecules, including ascorbic acid, α-tocopherol, β-carotene, reduced glutathione, uric acid, and bilirubin. The sum of endogenous and food-derived antioxidants represents the total antioxidant activity of the extracellular fluid. Cooperation of all the different antioxidants provides greater protection against attack by reactive oxygen or nitrogen radicals, than any single compound alone. Thus, the overall antioxidant capacity may give more relevant biological information compared to that obtained by the measurement of individual components, as it considers the cumulative effect of all antioxidants present in plasma and body fluids. The capacity of the antioxidants in the sample to prevent ABTS oxidation is compared with that of Trolox, a water-soluble tocopherol analogue, and is quantified as molar Trolox equivalents.

Anti-Oxidant capacity kit #709001 from Cayman Chemical (Ann Arbor, Mich. USA) was used as an in vitro bioassay to measure the total anti-oxidant capacity of each of the extracts identified in Table 1. The protocol was followed according to manufacturer recommendations. The assay relied on antioxidants in the sample to inhibit the oxidation of ABTS® (2,2'-azino-di-[3-ethylbenzthiazoline sulphonate]) to ABTS®.+ by metmyoglobin. The capacity of the antioxidants in the sample to prevent ABTS oxidation was compared with that Trolox, a water-soluble tocopherol analogue, and was quantified as a molar Trolox equivalent.

Tyrosinase Activity Assay:

In mammalian cells, tyrosinase catalyzes two steps in the multi-step biosynthesis of melanin pigments from tyrosine (and from the polymerization of dopachrome). Tyrosinase is localized in melanocytes and produces melanin (aromatic quinone compounds) that imparts color to skin, hair, and eyes.

Purified mushroom tyrosinase (Sigma) was incubated with its substrate L-Dopa (Fisher) in the presence or absence of each of the extracts in Table 1. Pigment formation was evaluated by colorimetric plate reading at 490 nm. The percent inhibition of mushroom tyrosinase activity was calculated compared to non-treated controls to determine the ability of test extracts to inhibit the activity of purified enzyme. Test extract inhibition was compared with that of kojic acid (Sigma).

The apparatus disclosed and claimed in this specification can be made and executed without undue experimentation in light of the present disclosure. While the apparatus has been described in terms of particular embodiments, it will be apparent to those of skill in the art that variations may be applied to the apparatus and methods for its use without departing from the concept, spirit and scope of the invention.

The invention claimed is:

1. A method of treating human skin with acne thereon, the method consisting essentially of:
   (i) obtaining an apparatus consisting essentially of:
      (a) a water-permeable absorbent material, wherein the water-permeable absorbent material is a sponge, cloth, or mesh which has a first outer surface and a second outer surface; and
      (b) a plant material, a plant extract, or a combination thereof,
      wherein the plant material, the plant extract, or the combination thereof is stitched, or sealed, or stitched and sealed within the water-permeable absorbent material, and wherein the water-permeable absorbent material is configured to absorb water and allow the absorbed water to contact the plant material, the plant extract, or the combination thereof so as to release, solubilize, or release and solubilize a water-soluble skin-active ingredient from the plant material, from the plant extract, or from the combination thereof and allow the water-soluble skin-active ingredient to be absorbed by the absorbent material;
   (ii) placing the apparatus in water heated to 30° C. to 100° C. for a sufficient period of time so as to release, solubilize, or release and solubilize the water-soluble skin-active ingredient from the plant material, from the plant extract, or from the combination thereof, and for a sufficient period of time to allow said water-soluble skin-active ingredient to be absorbed by the water-permeable absorbent material to yield a treated apparatus; and
   (iii) contacting the human skin with acne thereon with the treated apparatus to treat the acne.

2. The method of claim 1, wherein the sufficient period of time is 1 minute to 60 minutes.

3. The method of claim 1, wherein the sufficient period of time is 1 minute to 30 minutes.

4. The method of claim 1, wherein the sufficient period of time is 10 minutes to 30 minutes.

5. The method of claim 1, wherein the first outer surface is configured to exfoliate skin and the second outer surface is configured to not exfoliate skin.

6. The method of claim 1, wherein the plant material, plant extract or combinations thereof are dried plant material, dried plant extract, or a combination of dried plant material and dried plant extract.

7. The method of claim 1, wherein the water content of the apparatus is less than 1% by weight of the apparatus before the step of placing the apparatus in water.

8. The method of claim 1, wherein the apparatus is shaped to substantially correspond to a T-zone region of facial skin.

9. The method of claim 1, wherein the apparatus is shaped to substantially correspond to a S-zone region of facial skin.

10. The method of claim 1, wherein the apparatus is shaped to substantially correspond to an O-zone region of facial skin.

11. The method of claim 1, wherein the apparatus is shaped to substantially correspond to the eye area region of facial skin.

12. The method of claim 1, wherein said first outer surface has a greater surface roughness when compared with the surface roughness of the second outer surface.

13. The method of claim 1, wherein the apparatus does not include a paraben, chlorobutanol, a phenol, sorbic acid, or thimerosal.

14. The method of claim 1, wherein the water-soluble skin-active ingredient of the apparatus also treats fine lines, wrinkles, discolored skin, erythemic skin, or a combination thereof.

\* \* \* \* \*